United States Patent [19]
Keller et al.

[11] Patent Number: 5,969,072
[45] Date of Patent: Oct. 19, 1999

[54] SILYL AND SILOXYL SUBSTITUTED CARBORANES WITH UNSATURATED ORGANIC END GROUPS

[75] Inventors: Teddy M. Keller, Fairfax Station; Eric J. Houser, Springfield, both of Va.

[73] Assignee: The United States of America as represented by the Secretary of the Navy, Washington, D.C.

[21] Appl. No.: 09/031,997

[22] Filed: Feb. 27, 1998

[51] Int. Cl.[6] .................................................. C08G 77/56
[52] U.S. Cl. ............................. 528/5; 556/403; 556/431; 556/433; 528/25
[58] Field of Search ................... 556/403, 431, 556/433; 528/5, 25

[56] References Cited

U.S. PATENT DOCUMENTS

| | | | |
|---|---|---|---|
| 5,272,237 | 12/1993 | Keller et al. | 528/5 |
| 5,679,818 | 10/1997 | Bucca et al. | 556/403 |
| 5,807,953 | 9/1998 | Bucca et al. | 528/5 |

*Primary Examiner*—Melvyn I. Marquis
*Attorney, Agent, or Firm*—Thomas E. McDonnell; Ralph T. Webb

[57] ABSTRACT

Carborane-silane/siloxane compounds having unsaturated organic end groups are represented by the formula:

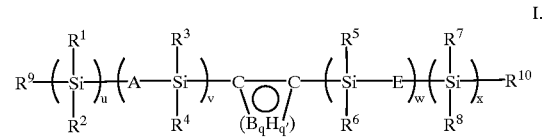

wherein: u and x are independently selected positive integers, v and w are independently selected integers greater than or equal to zero, $R^1$, $R^2$, $R^3$, $R^4$, $R^5$, $R^6$, $R^7$ and $R^8$ are independently selected from the group consisting of alkyl, aryl, alkylaryl, haloalkyl, haloaryl and mixtures thereof; A and E are independently selected from the group consisting of O, an aliphatic bridge, an aryl bridge and mixtures thereof; and $R^9$ and $R^{10}$ are unsubstituted or substituted vinyl or ethynyl groups.

17 Claims, No Drawings

SILYL AND SILOXYL SUBSTITUTED CARBORANES WITH UNSATURATED ORGANIC END GROUPS

BACKGROUND OF THE INVENTION

1. Field of the Invention

The invention relates generally to carborane-silane/siloxane compounds and in particular to carborane-silane/siloxane compounds having unsaturated organic end groups.

2. Description of the Related Art

The search for high temperature oxidatively stable materials has led to the development of organoboron polymers, particularly silyl or siloxyl polymers containing carboranyl and acetylenic groups incorporated into the polymer backbone. Polymers that include carboranyl, silyl or siloxyl and acetylenic groups in the same polymeric chain combine the desirable features of both inorganics and organics: the carborane groups provide thermal and oxidative stability, the silane or siloxane groups provide chain flexibility and the acetylenic groups allow cross-linking of adjacent polymer strands to form thermosets. The acetylene groups remain inactive at lower temperatures and react either thermally or photochemically to form conjugated polymeric cross-links without the evolution of volatiles. Carborane-silane/siloxane-acetylene polymers have the advantage of being extremely easy to process and convert into thermosets or ceramics since they are either liquids at room temperature or low melting solids and are soluble in most organic solvents. The polymers are thus well-suited to serve as ceramic or thermoset polymeric precursors.

Thermoset polymers that include carborane, silane or siloxane and acetylene units are disclosed in U.S. Pat. No. 5,272,237; U.S. Pat. No. 5,292,779; U.S. Pat. No. 5,348,917; U.S. Pat. No. 5,483,017, and U.S. Pat. No. 5,681,870, each incorporated herein by reference in its entirety and for all purposes. The thermoset polymers described in U.S. Pat. Nos. 5,272,237; 5,292,779 and 5,348,917 are made from linear polymer precursors that include repeating units containing carborane-silane/siloxane-acetylene or related groups. The thermoset polymers described in U.S. Pat. No. 5,483,017 are made from linear polymer precursors that include, on each strand, both repeating units of carborane-silane/siloxane-acetylene or related groups and repeating units of siloxane/silane-acetylene or related groups. U.S. Pat. No. 5,681,870 describes a linear polymer with randomly distributed carborane, silane/siloxane and acetylene units. U.S. Pat. No. 5,348,917, U.S. Pat. No. 5,483,017 and U.S. Pat. No. 5,681,870 further disclose boron-carbon-silicon ceramics made by pyrolyzing carborane-silane/siloxane-acetylene thermoset polymers.

While these polymers show outstanding thermal and thermo-oxidative stabilities, their use is limited due to the high cost and limited availability of carboranes and the high cost of dilithiated acetylenes used in making the polymers.

U.S. Pat. No. 5,679,818, incorporated herein by reference, describes compounds of the formula $R^1$—$Ac^1$—$Ar^1$—M—$Ar^2$—$Ac^2$—$R^2$, wherein M is a silyl/siloxyl substituted carborane, $Ar^1$ and $Ar^2$ are aromatic groups, and $Ac^1$ and $Ac^2$ are alkynyl groups. The compounds are described as being useful as precursors for thermosets. Synthesis of these compounds involves the steps of attaching aromatic groups $Ar^1$ and $Ar^2$ to the silyl/siloxyl group and then attaching the alkynyl-containing groups $R^1$—$Ac^1$— and $R^2$—$Ac^2$— to the aromatic groups.

SUMMARY OF THE INVENTION

Silyl or siloxyl substituted carboranes have now been made with unsaturated organic end groups attached directly to the silanes or siloxanes on the terminal ends of the compounds. These compounds can be made by a relatively simple reaction scheme and can be used to form thermosets and ceramics or can be crosslinked with other compounds such as hydrosilanes and hydrosiloxanes to form polymeric systems exhibiting superior mechanical strength and thermal/oxidative stability.

Accordingly, the invention is directed to a compound of the formula:

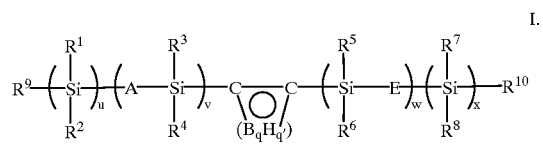

wherein:

(1) u and x are independently selected positive integers;

(2) v and w are independently selected integers greater than or equal to zero;

(3) $R^1$, $R^2$, $R^3$, $R^4$, $R^5$, $R^6$, $R^7$ and $R^8$ are independently selected from the group consisting of alkyl, aryl, alkylaryl, haloalkyl, haloaryl and mixtures thereof;

(4)

represents a carboranyl group wherein q and q' are integers from 3 to 16;

(5) A and E are independently selected from the group consisting of O, an aliphatic bridge, an aryl bridge and mixtures thereof; and (6) $R^9$ and $R^{10}$ are independently selected from the group consisting of

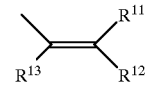

wherein $R^{11}$, $R^{12}$ and $R^{13}$ are independently selected and are H, alkyl, aryl or silyl and

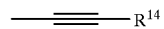

wherein $R^{14}$ is H, alkyl, aryl or silyl.

DETAILED DESCRIPTION OF THE PREFERRED EMBODIMENTS

The invention relates to carborane-silane/siloxane compounds having unsaturated organic end groups, as represented by the formula:

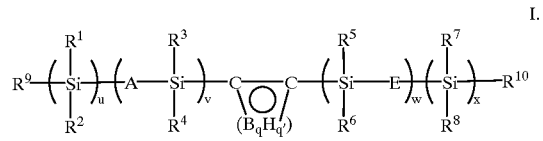

wherein: u and x are independently selected positive integers, v and w are independently selected integers greater than or equal to zero, $R^1$, $R^2$, $R^3$, $R^4$, $R^5$, $R^6$, $R^7$ and $R^8$ are independently selected from the group consisting of alkyl, aryl, alkylaryl, haloalkyl, haloaryl and mixtures thereof; A and E are independently selected from the group consisting of O, an aliphatic bridge, an aryl bridge and mixtures thereof, and $R^9$ and $R^{10}$ are independently selected from the group consisting of

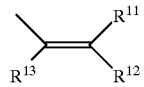

wherein $R^{11}$, $R^{12}$ and $R^{13}$ are independently selected and are H, alkyl, aryl or silyl, and

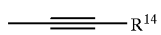

wherein $R^{14}$ is H, alkyl, aryl or silyl.

Particular values for u, v, w and x, and particular choices for the side chains $R^1$, $R^2$, $R^3$, $R^4$, $R^5$, $R^6$, $R^7$, $R^8$, the linking groups A and E and the end groups $R^9$, $R^{10}$, $R^{11}$, $R^{12}$, $R^{13}$ and $R^{14}$ may be selected according to particular properties desired for the compound and for polymers made using the compound. For example, increasing the number of silane or siloxane groups (increasing u, v, w and x) would lower the melting point of the compound and increase the chain flexibility. Using larger alkyl groups for the side chains $R^1$, $R^2$, $R^3$, $R^4$, $R^5$, $R^6$, $R^7$, $R^8$ would increase the solubility of the compound in organic solvents and increase the hydrophobicity and decrease the thermo-oxidative stability of polymers made using the compound. Using aryl groups for the side chains $R^1$, $R^2$, $R^3$, $R^4$, $R^5$, $R^6$, $R^7$, $R^8$ would increase the stiffness and slightly increase the thermo-oxidative stability of polymers made using the compound. Using aryl linking groups for A and E would add considerable stiffness to polymers made from the compound, but would decrease the thermo-oxidative stability as compared to using oxygen for the linking group. Using alkyl groups for A and E would give similar mechanical properties as using oxygen, but would result in a decreased thermo-oxidative stability.

The selection of particular end groups for $R^9$ and $R^{10}$ and the particular choices for $R^{11}$, $R^{12}$, $R^{13}$ and $R^{14}$ affect the rate of hydrosilation and curing of the compound. For example, vinyl groups typically cure faster than ethynyl groups. The choice between vinyl and ethynyl groups also affects the mechanical properties and thermo-oxidative stability of cross-linked polymers made using the compound. The use of vinyl-terminated monomers results in a crosslinked polymer connected by alkyl linkages whereas the use of ethynyl terminated monomers results in a crosslinked polymer connected by vinyl linkages. Typically, the crosslinked polymers made using vinyl monomers are less brittle and have lower oxidative stability than those made using ethynyl monomers. Using ethynyl-terminated monomers allows for additional thermal crosslinking of residual acetylene end groups.

The vinyl and ethynyl groups may be unsubstituted or may be substituted at $R^{11}$, $R^{12}$, $R^{13}$ or $R^{14}$ with alkyl, aryl or silyl groups. If substituted, the preferred groups are methyl, phenyl or trimethylsilyl. Compounds wherein $R^{11}$, $R^{12}$, $R^{13}$ or $R^{14}$ are alkyl, aryl or silyl will typically have slower curing times and less oxidative stability than compounds wherein $R^{11}$, $R^{12}$, $R^{13}$ and $R^{14}$ are H.

In the structure above,

represents any carboranyl group wherein q and q' are independently selected integers from 3 to 16. Preferably, the carboranyl group is selected from the group consisting of 1,7-dodecacarboranyl; 1,10-octacarboranyl; 1,6-octacarboranyl; 2,4-pentacarboranyl; 1,6-tetracarboranyl; 9-alkyl-1,7-dodecacarboranyl; 9,10-dialkyl-1,7-dodecacarboranyl; 2-alkyl-1,10-octacarboranyl; 8-alkyl-1,6-octacarboranyl; decachloro-1,7-dodecacarboranyl; octachloro-1,10-octacarboranyl; decafluoro-1,7-dodecacarboranyl; octafluoro-1,10-octacarboranyl; closo-dodeca-ortho-carboranyl; closo-dodeca-meta-carboranyl; closo-dodeca-para-carboranyl. The selection of a particular carborane affects the mechanical properties and environmental stability of the compound and polymers made using the compound. Most preferably, q and q' in the above formula are equal to 10.

Preferably, the compounds of the present invention are either (1) silane compounds wherein, in the above formula I, v and w are both zero, u and x are equal integers between 1 and 10, inclusive, $R^1$, $R^2$, $R^7$ and $R^8$ are $CH_3$ groups or (2) siloxane compounds wherein, in the above formula I, u and x in the above formula are both 1, v and w are equal integers between 1 and 10, inclusive, A and E are both oxygen and $R^1$, $R^2$, $R^3$, $R^4$, $R^5$, $R^6$, $R^7$, $R^8$ are $CH_3$ groups.

In one specific embodiment, the present invention comprises a compound of the formula:

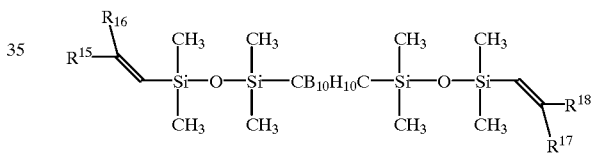

wherein at least one of $R^{15}$ and $R^{16}$ is H and the other is H or methyl, and wherein at least one of $R^{17}$ and $R^{18}$ is H and the other is H or methyl.

In another specific embodiment, the present invention comprises a compound of the formula:

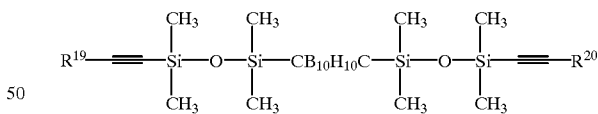

wherein $R^{19}$ and $R^{20}$ are both H or are both phenyl.

The starting material for making compounds of formula I is a carborane-silane/siloxane compound of the formula

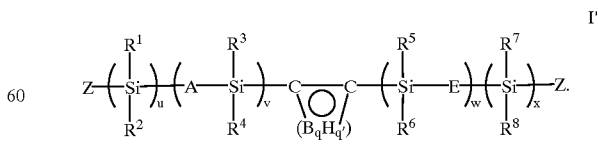

wherein u, v, w, x, $R^1$, $R^2$, $R^3$, $R^4$, $R^5$, $R^6$, $R^7$, $R^8$, A and E, are as defined above and wherein Z is Cl, Br, I, F, $CF_3SO_3$, $CH_3SO_3$, $CF_3CH_2SO_3$, $C_6H_6SO_3$, or $CH_3SiOSO_3$. Compound I' may be reacted with Grignard reagents vinylmagnesium bromide or ethynylmagnesium bromide to replace the Z groups with vinylic or acetylenic end groups. Alternatively, a metalated vinylic or acetylenic reagent, such as lithiated ethylenes or acetylenes may be used. These may be unsubstituted or substituted. For example, lithiophenylacetylene may be used to attach phenylacetylene end groups.

The Z-substituted carborane-silane/siloxane compounds of formula I' may be readily synthesized using methods known in the art, particularly by methods described in U.S. Pat. No. 5,272,237, U.S. Pat. No. 5,292,779, U.S. Pat. No. 5,348,917 and U.S. Pat. No. 5,483,017, each incorporated by reference above. Chlorinated carborane-silane/siloxane compounds are commercially available from Dexsil Corporation, Hamden, Conn. Of course, skilled practitioners will be able to modify the foregoing synthetic routes, using the knowledge of a person of ordinary skill in the art.

The carborane-silane/siloxane compounds of the formula I may be used in a variety of cross-linking and polymerization reactions. In particular, the compounds of formula I may be combined with a silicon hydride-containing organosilicon compound that contains two or more silicon hydride moieties per molecule and a hydrosilation catalyst to form a precursor composition, and the precursor composition may then be allowed to cure to form a crosslinked polymer system or a thermoset polymer system. Preferably, the silicon hydride-containing organosilicon compound is a hydrosilane or hydrosiloxane containing polymer such as poly(methylhydrosiloxane) or poly(methylhydrosilane) or a copolymer made up of dimethylsiloxane and methylhydrosiloxane units. The silicon hydride-containing organosilicon compound may also be a smaller molecule containing silicon hydride moieties, such as phenyltris(dimethylsiloxy) silane.

The reaction of a carborane-silane/siloxane compound having vinyl groups with a silicon hydride-containing organosilicon compound having at least two silicon hydride moieties in the presence of a hydrosilation catalyst to form a crosslinked polymer system is illustrated by the following reaction scheme, wherein the carborane-silane/siloxane compound is 1,7-bis(vinyltetramethyldisiloxyl)-m-carborane and the silicon hydride-containing organosilicon compound is poly(methylhydrosiloxane):

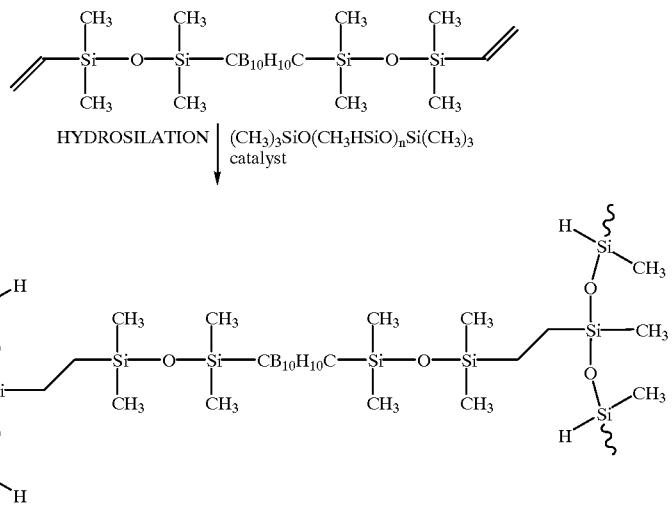

The reaction of a carborane-silane/siloxane compound having ethynyl groups to react with a silicon hydride-containing organosilicon compound having at least two silicon hydride moieties in the presence of a hydrosilation catalyst to form a crosslinked polymer system is illustrated by the following reaction scheme, wherein the carborane-silane/siloxane compound is 1,7-bis(ethynyltetramethyldisiloxyl)-m-carborane and the silicon hydride-containing organosilicon compound is poly(methylhydrosiloxane):

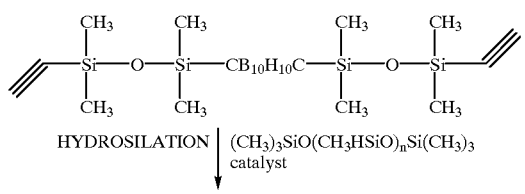

-continued

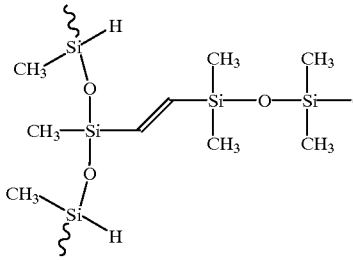
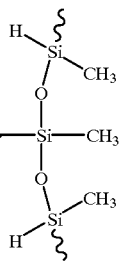

The formation of crosslinked polymer systems as described above may also be carried out by using mixtures of more than one compound of formula I and/or more than one silicon hydride-containing organosilicon compound, each having at least two silicon hydride moieties per molecule.

The catalyst may be any hydrosilation catalyst known in the art. Typically, the catalyst is a metal containing catalyst, such as, for example, a platinum catalyst. Selection of a particular catalyst will depend on the particular silicon hydride-containing organosilicon compound and the particular compounds of formula I used in the hydrosilation reaction. A comprehensive discussion of hydrosilation reactions and the selection of catalysts is found in Marciniec, Bodgan, ed., Comprehensive Handbook on Hydrosilylation, Pergamon Press, Oxford, N.Y., 1992, incorporated herein by reference.

In forming the precursor composition, the compound of formula I, the silicon hydride-containing organosilicon compound and the catalyst may be mixed by any method known in the art. The hydrosilation reaction may be carried out in the absence of a solvent, or in the presence of an organic solvent that is inert to reaction with the catalyst. The reaction will typically proceed faster in the presence of a solvent. Suitable solvents include, but are not limited to toluene, butanol, THF, diethyl ether and hydrocarbons.

The mechanical properties and thermo-oxidative stability of the crosslinked polymer system will be affected by the relative amount of the compound of formula I used in comparison to the number of silicon hydride moieties in the silicon hydride-containing organosilicon compound available for bonding. For vinyl compounds, the optimum ratio of silicon hydride moieties to vinyl groups is from about 1:1 to about 3:1. The optimum ratio of silicon hydride moieties to ethynyl groups can be greater since ethynyl groups can participate in several types of crosslinking reactions.

The hydrosilation reaction may be carried out either under ambient conditions or at elevated temperatures. In general, the reaction proceeds faster as the temperature is increased. However, if a thermally unstable hydrosilation catalyst is used the reaction is slowed or stopped by heating. To form a crosslinked polymer, the compound of formula I is reacted with the silicon hydride-containing compound at a temperature of between about 25° C. and about 100° C.

Thermoset polymers may be created by heating the precursor composition to a temperature of between about 100° C. and about 500° C. Particularly when the carborane monomer of formula I is an acetylene compound, heating in this temperature range causes the reaction mixture to undergo additional crosslinking reactions. The thermoset polymer created thereby has excellent thermal and oxidative stability and may be useful for high temperature structural and coating applications.

Additional crosslinking can also be achieved by exposing the precursor composition to ultraviolet light. Because of the limited penetration of light into a polymer composition, the use of photocrosslinking to form thermoset polymers according to the present invention will be generally limited to films or coatings.

The crosslinked polymers and thermosets described above can be pyrolyzed to create ceramics having excellent thermal stability. The boron-carbon-silicon ceramics are made by forming a crosslinked polymer or thermoset as described above and then pyrolyzing the polymer or thermoset to form a boron-carbon-silicon ceramic. The pyrolysis is accomplished typically by heating the crosslinked polymer or thermoset in an inert atmosphere such as $N_2$ at a temperature between about 500° C. and about 2750° C., or by heating the crosslinked polymer or thermoset in an oxidizing atmosphere such as air at a temperature between about 500° C. and about 1650° C. The boron content of the boron-carbon-silicon ceramic can be varied and controlled by varying the molar ratio of the compound of formula I to the silicon hydride-containing organosilicon compound in the precursor composition.

The use of the compounds of the present invention to create crosslinked polymers, thermosets and ceramics is further described in the U.S. patent application Ser. No. 09/031,583, entitled "POLYMER PRECURSOR COMPOSITION, CROSSLINKED POLYMERS, THERMOSETS AND CERAMICS MADE WITH SILYL AND SILOXYL SUBSTITUTED CARBORANES WITH UNSATURATED ORGANIC END GROUPS" having the same inventors and the same filing date as the present application and incorporated herein by reference.

EXAMPLES

Having described the invention, the following examples are given to illustrate specific applications of the invention including the best mode now known to perform the invention. These specific examples are not intended to limit the scope of the invention described in this application.

General Comments

All reactions were carried out under an inert atmosphere using standard Schlenk techniques unless otherwise noted. Tetrahydrofuran (THF) was distilled from sodium/benzophenone under $N_2$ immediately prior to use. Vinylmagnesium bromide and ethynylmagnesium bromide were purchased from Aldrich Chemical Co. and used as received. Bis-1,7-(chlorotetramethyldisiloxyl)-m-carborane was purchased from Dexsil Corp. and used as received. Poly (methylhydrosiloxane) (approx. mol. wt. 2700, trimethylsilyl terminated) and the (methylhydrosiloxane/dimethylsiloxane) copolymer made up of about 50–55% methylhydrosiloxane units and about 45–50% dimethylsiloxane units were purchased from United Technologies and used as received. Chloroplatinic acid hexahydrate was purchased from Strem Chemical Co. and used as received. All other chemicals were of reagent grade.

Thermogravimetric analyses (TGA) were performed on a TA Instruments SDT 2960 Simultaneous DTA-TGA thermogravimetric analyzer. Differential scanning calorimetry (DSC) experiments were performed on a DuPont 910 instrument. All thermal measurements were carried out at a heating rate of 10° C./min and a gas flow rate of 60 mL/min. Infrared spectra were recorded using a Nicolet Magna 750 FTIR spectrometer. $^1$H and $^{13}$C NMR spectra were recorded on a Bruker AC-300 NMR spectrometer in $CDCl_3$.

Example 1

Synthesis of 1,7-bis(vinyltetramethyldisiloxyl)-m-carborane, 1

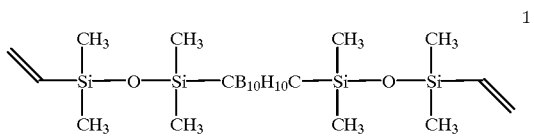

A 250 mL Schlenk flask containing 1,7-bis(chlorotetramethyldisiloxyl)-m-carborane (21.08 g, 44.15 mmol) in THF (50 mL) was cooled in an ice bath. The solution was then treated with 89 mL of 1.0 M vinylmagnesium bromide (89 mmol) which was added slowly via syringe. After the addition was complete, the cold bath was removed and the resulting solution was allowed to stir at room temperature for two hours. The solution was quenched by addition of $Me_3SiCl$ (2–3 mL) and stirred for 30 minutes at room temperature. The reaction was then treated with diethyl ether (20 mL) and cold, saturated aqueous $NH_4Cl$ (30 mL). The organic layer was separated and the aqueous portion extracted with ether (2×20 mL). The organic extracts were combined, dried over anhydrous $MgSO_4$, and the solution filtered through Celite. After removal of volatiles (water aspiration), the crude product was purified by column chromatography (two times, $SiO_2$) eluting with hexanes. Evaporation of solvent left pure 1 (18.51 g, 91%). Elem. Calcd. for $C_{14}H_{40}B_{10}Si_4O_2$: C, 36.48; H, 8.75; B, 23.46; Si, 24.37. Found: C, 36.31; H, 8.63; B, 23.14: Si, 24.03. IR (KBr, cm$^{-1}$): 3052 ($v_{C-H}$, —$C_2H_3$), 2961 ($v_{C-H}$, Si—$CH_3$), 2596 ($v_{B-H}$), 1596 ($v_{CH=CH2}$), 1408 ($v_{=CH2\ bend}$), 1259 ($v_{Si-C}$), 1078 ($v_{Si-O}$), 794 ($v_{Si-C\ bend}$). $^1$H NMR ($CDCl_3$, ppm): 0.167 (Si—$CH_3$), 0.169 (Si—$CH_3$), 5.681 (—$C_2H_3$), 5.695 (—$C_2H_3$), 5.748 (—$C_2H_3$), 5.761 (—$C_2H_3$), 5.918 (—$C_2H_3$), 5.934 (—$C_2H_3$), 5.968 (—$C_2H_3$), 5.983 (—$C_2H_3$), 6.046 (—$C_2H_3$), 6.095 (—$C_2H_3$), 6.112 (—$C_2H_3$), 6.162 (—$C_2H_3$). $^{13}C\{^1H\}$ NMR ($CDCl_3$, ppm): 0.14 (Si—$CH_3$), 0.56 (Si—$CH_3$), 68.49 (m—$C_2B_{10}H_{10}$), 132.16 (—$C_2H_3$), 138.61 (—$C_2H_3$).

Example 2

Synthesis of 1,7-bis(ethynyltetramethyldisiloxyl)-m-carborane, 2

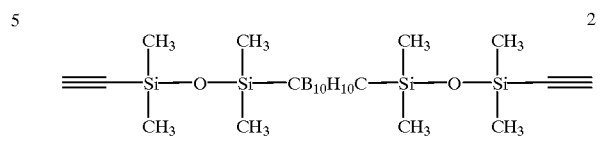

A 250 mL Schlenk flask containing 1,7-bis(chlorotetramethyldisiloxyl)-m-carborane (15.81 g, 33.11 mmol) in THF (30 mL) was cooled in an ice bath. The solution was then treated with 133 mL of 0.5 M ethynylmagnesium bromide (66.5 mmol) which was added slowly via syringe at 0° C. The cold bath was removed and the resulting solution was allowed to stir at room temperature for two hours. The reaction was quenched by addition of $Me_3SiCl$ (2–3 mL) and the organics removed by aqueous extraction with diethyl ether and dried over $MgSO_4$. After removal of volatiles in vacuo (water aspiration), the crude product was purified by column chromatography (two times, $SiO_2$) by eluting with hexanes. Evaporation of solvent left pure 2 (12.41 g, 82%). IR (KBr, cm$^{-1}$): 3290 (vC—H, —$C_2H$), 2964 (vC—H, Si—$CH_3$), 2596 (vB—H), 2039 (vCC), 1260 (vSi—C), 1080 (vSi—O), 798 (Si—C bend). $^1$H NMR ($CDCl_3$, ppm): 0.23 (Si—$CH_3$), 0.27 (Si—$CH_3$), 2.41 (—$C_2H$). $^{13}C\{^1H\}$ NMR ($CDCl_3$, ppm): 0.25 (Si—$CH_3$), 1.89 (Si—$CH_3$), 68.15 (m—$C_2B_{10}H_{10}$), 88.58 (—CCH), 92.64 (—CCH).

General Comments on Hydrosilation Reactions

A solution of 0.05 M $H_2PtCl_6.6H_2O$ in THF was prepared by dissolution of 0.26 g of $H_2PtCl_6.6\ H_2O$ in 10 mL of THF. This catalyst solution was used in all hydrosilation reactions. Poly(methylhydrosiloxane), 3, was reacted with monomers 1 and 2 via hydrosilation reactions. Polymers derived from monomer 1 are labeled as 4x, and polymers derived from monomer 2 are labeled as 5x. A (methylhydrosiloxane/dimethylsiloxane) copolymer, 6, made up of about 50–55% methylhydrosiloxane units and about 45–50% dimethylsiloxane units was also reacted with monomers 1 and 2 via hydrosilation reactions. Polymers derived from 6 and 1 are labeled as 7x, and polymers derived from 6 and 2 are labeled as 8x.

Example 3

Hydrosilation Reactions of 1,7-bis(vinyltetramethyldisiloxyl)-m-carborane, 1 with poly(methylhydrosiloxane), 3

Polymer 4a: To a small reaction vial was added 0.20 g (0.434 mmol) of 1,7-bis(vinyltetramethyldisiloxyl)-m-carborane, 1 and 0.054 g (0.024 mmol) of poly(methylhydrosiloxane), 3. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a hard, colorless solid. IR (KBr, cm$^{-1}$): 2960 ($v_{C-H}$), 2911 ($v_{C-H}$), 2598 ($v_{B-H}$), 1409 ($v_{C-H\ bend}$), 1260 ($v_{Si-C}$), 1080 ($v_{Si-O}$), 791 ($v_{Si-C}$).

Polymer 4b: To a small reaction vial was added 0.20 g (0.434 mmol) of 1,7-bis(vinyltetramethyldisiloxyl)-m-carborane, 1 and 0.106 g (0.047 mmol) of poly(methylhydrosiloxane), 3. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a hard, colorless solid.

Polymer 4c: To a small reaction vial was added 0.20 g (0.434 mmol) of 1,7-bis(vinyltetramethyldisiloxyl)-m-carborane, 1 and 0.205 g (0.090 mmol) of poly (methylhydrosiloxane), 3. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a hard, colorless solid.

Polymer (film) 4d: A film was cast from a toluene solution (2 mL) containing 0.40 g (0.868 mmol) of 1,7-bis (vinyltetramethyldisiloxyl)-m-carborane, 1 and 0.156 g (0.069 mmol) of poly(methylhydrosiloxane), 3. The solution was treated with 2 drops of 0.05 M $H_2PtCl_6.6H_2O$ in THF added from a 500 μL syringe. The solution was poured onto a watchglass and allowed to stand overnight at room temperature. This left a brittle, colorless film. IR (KBr, cm$^{-1}$): 2961 ($v_{C-H}$), 2911 ($v_{C-H}$), 2598 ($v_{B-H}$), 2160 ($v_{Si-H}$), 1409 ($v_{C-H\ bend}$), 1260 ($v_{Si-C}$), 1080 ($v_{Si-O}$), 791 ($v_{Si-C}$).

Example 4
Hydrosilation Reactions of 1,7-bis (ethynyltetramethyldisiloxyl)-m-carborane, 2 with poly (methylhydrosiloxane), 3

Polymer 5a: To a small reaction vial was added 0.20 g of 1,7-bis(ethynyltetramethyldisiloxyl)-m-carborane, 2 and 0.052 g of poly(methylhydrosiloxane), 3. The contents were mixed and treated with one drop of 0.05 M $H_2PtCl_6.6H_2O$ in THF added from a 500 μL syringe. The reactants were mixed by shaking the vial and the reaction was allowed to stand at room temperature for 12 days. The sample was then heated to 100° C. for 3 days giving a hard, colorless solid.

Polymer 5b: To a small reaction vial was added 0.20 g of 1,7-bis(ethynyltetramethyldisiloxyl)-m-carborane, 2 and 0.103 g of poly(methylhydrosiloxane), 3. The contents were mixed and treated with one drop of 0.05 M $H_2PtCl_6.6H_2O$ in THF added from a 500 μL syringe. The reactants were mixed by shaking the vial and the reaction was allowed to stand at room temperature for 12 days. The sample was then heated to 100° C. for 3 days giving a hard, colorless solid.

Polymer 5c: To a small reaction vial was added 0.20 g of 1,7-bis(ethynyltetramethyldisiloxyl)-m-carborane, 2 and 0.205 g of poly(methylhydrosiloxane), 3. The contents were mixed and treated with one drop of 0.05 M $H_2PtCl_6.6H_2O$ in THF added from a 500 μL syringe. The reactants were mixed by shaking the vial and the reaction was allowed to stand at room temperature for 12 days. The sample was then heated to 100° C. for 3 days giving a hard, colorless solid.

Example 5
Hydrosilation Reactions of 1,7-bis (vinyltetramethyldisiloxyl)-m-carborane, 1 with (methylhydrosiloxane/dimethylsiloxane) copolymer, 6

Polymer 7a: To a small reaction vial was added 0.20 g (0.434 mmol) of 1,7-bis(vinyltetramethyldisiloxyl)-m-carborane, 1 and 0.10 g of(methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a colorless solid.

Polymer 7b: To a small reaction vial was added 0.20 g (0.434 mmol) of 1,7-bis(vinyltetramethyldisiloxyl)-m-carborane, 1 and 0.20 g of (methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a colorless solid.

Polymer 7c: To a small reaction vial was added 0.20 g (0.434 mmol) of 1,7-bis(vinyltetramethyldisiloxyl)-m-carborane, 1 and 0.40 g of(methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 10 days at room temperature during which time the contents turned to a colorless solid.

Example 6
Hydrosilation Reactions of 1,7-bis (ethynyltetramethyldisiloxyl)-m-carborane, 2 with (methylhydrosiloxane/dimethylsiloxane) copolymer, 6

Polymer 8a: To a small reaction vial was added 0.20 g (0.434 mmol) of 1,7-bis(ethynyltetramethyldisiloxyl)-m-carborane, 2 and 0.102 g of (methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 12 days at room temperature during which time the contents gelled. The sample was then heated to 100° C. for 3 days giving a hard, colorless solid.

Polymer 8b: To a small reaction vial was added 0.20 g (0.434 mmol) of 1,7-bis(ethynyltetramethyldisiloxyl)-m-carborane, 2 and 0.203 g of (methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 12 days at room temperature during which time the contents gelled. The sample was then heated to 100° C. for 3 days giving a hard, colorless solid.

Polymer 8c: To a small reaction vial was added 0.208 g (0.434 mmol) of 1,7-bis(ethynyltetramethyldisiloxyl)-m-carborane, 2 and 0.402 g of (methylhydrosiloxane/dimethylsiloxane) copolymer, 6. The contents were mixed and treated with one drop of 0.05 M $H_2PtCl_6.6\ H_2O$ in THF added from a 500 μL syringe. The reactants were mixed by vigorous shaking and the reaction was allowed to stand for 12 days at room temperature during which time the contents gelled. The sample was then heated to 100° C. for 3 days giving a hard, colorless solid.

Example 7
Synthesis of 1,7-bis(phenylacetylenetetramethyldisiloxyl)-m-carborane

Phenylacetylene is reacted with one equivalent of butyllithium at −78° C. to give lithiophenylacetylene. Two equivalents of lithiophenylacetylene are reacted with 1,7-bis(chlorotetramethyldisiloxyl)-m-carborane to give 1,7-bis (phenylacetylenetetramethyldisiloxyl)-m-carborane. This latter material can be used in the hydrosilation reaction as 1,7-bis(ethynyltetramethyldisiloxyl)-m-carborane above.

Example 8
Synthesis of 1,7-bis(vinyldimethylsilyl)-m-carborane

Two equivalents of butyllithium are reacted with m-carborane to give 1,7-dilithiocarborane. Treatment of this product with two equivalents of vinyldimethylchlorosilane yields 1,7-bis(vinyldimethylsilyl)-m-carborane. 1,7-bis (vinyldimethylsilyl)-m-carborane can be reacted with poly (methylhydrosiloxane) via a hydrosilation reaction to yield a crosslinked siloxane.

Example 9

Formation of Ceramic

Polymer 5b was weighed into an alumina TGA sample pan and heated to 1500° C. at 10° C./min under a nitrogen atmosphere. This gave a hard, black ceramic with 71% char yield.

The resulting ceramic char was cooled to room temperature and then reheated to 1500° C. in air at 10° C./min. At 1500° C., the weight retention was 101%. The slight increase in weight is attributed to the formation of an oxide layer on the outer surface of the sample. Similar results were obtained for 5a and 5c. The results show the outstanding oxidative stability of the ceramic chars obtained from these polymers.

Obviously, many modifications and variations of the present invention are possible in light of the above teachings. It is therefore to be understood that, within the scope of the appended claims, the invention may be practiced otherwise than as specifically described.

What is claimed is:

1. A compound of the formula:

$$R^9 - \left( \underset{R^2}{\overset{R^1}{\underset{|}{\overset{|}{Si}}}} \right)_u - \left( A - \underset{R^4}{\overset{R^3}{\underset{|}{\overset{|}{Si}}}} \right)_v - C \underset{(B_qH_{q'})}{\overset{\diagdown O \diagup}{-}} C - \left( \underset{R^6}{\overset{R^5}{\underset{|}{\overset{|}{Si}}}} - E \right)_w \left( \underset{R^8}{\overset{R^7}{\underset{|}{\overset{|}{Si}}}} \right)_x - R^{10}$$

wherein:

(1) u and x are independently selected positive integers;
(2) v and w are independently selected integers greater than or equal to zero;
(3) $R^1$, $R^2$, $R^3$, $R^4$, $R^5$, $R^6$, $R^7$ and $R^8$ are independently selected from the group consisting of alkyl, aryl, alkylaryl, haloalkyl, haloaryl and mixtures thereof;

(4)

$$-C \underset{B_qH_{q'}}{\overset{\diagdown O \diagup}{-}} C-$$

represents a carboranyl group;

(5) q and q' are integers from 3 to 16;
(6) A and E are independently selected from the group consisting of O, an aliphatic bridge, an aryl bridge and mixtures thereof; and
(7) $R^9$ and $R^{10}$ are independently selected from the group consisting of $$\underset{R^{13}}{\overset{}{\diagdown}} = \underset{R^{12}}{\overset{R^{11}}{\diagup}}$$

wherein $R^{11}$, $R^{12}$ and $R^{13}$ are independently selected and are H, alkyl, aryl or silyl and $$\text{———}\equiv\text{———}R^{14}$$

wherein $R^{14}$ is H, alkyl, aryl or silyl.

2. The compound of claim 1 wherein the carboranyl group is selected from the group consisting of 1,7-dodecacarboranyl; 1,10-octacarboranyl; 1,6-octacarboranyl; 2,4-pentacarboranyl; 1,6-tetracarboranyl; 9-alkyl-1,7-dodecacarboranyl; 9,10-dialkyl-1,7-dodecacarboranyl; 2-alkyl-1,10-octacarboranyl; 8-alkyl-1,6-octacarboranyl; decachloro-1,7-dodecacarboranyl; octachloro-1,10-octacarboranyl; decafluoro-1,7-dodecacarboranyl; octafluoro-1,10-octacarboranyl; closo-dodeca-ortho-carboranyl; closo-dodeca-meta-carboranyl; closo-dodeca-para-carboranyl.

3. The compound of claim 1 wherein $R^1$, $R^2$, $R^7$ and $R^8$ are $CH_3$.

4. The compound of claim 3 wherein v and w are positive integers and $R^3$, $R^4$, $R^5$, and $R^6$ are $CH_3$.

5. The compound of claim 1 wherein v and w are positive integers and A and E are both oxygen.

6. The compound of claim 1 wherein q and q' are 10.

7. The compound of claim 1 wherein u and x are equal integers from 1 to 10, inclusive, and v=w=0.

8. The compound of claim 1 wherein u=x=1, and v and w are equal integers from 1 to 10, inclusive.

9. The compound of claim 1 wherein $R^1$, $R^2$, $R^7$ and $R^8$ are $CH_3$, u and x are equal integers from 1 to 10, inclusive, and v=w=0.

10. The compound of claim 1 wherein $R^1$, $R^2$, $R^3$, $R^4$, $R^5$, $R^6$, $R^7$ and $R^8$ are $CH_3$, A and E are oxygen, u=x=1, and v and w are equal integers from 1 to 10, inclusive.

11. The compound of claim 1 wherein $R^9$ and $R^{10}$ are both $$\underset{R^{13}}{\overset{}{\diagdown}} = \underset{R^{12}}{\overset{R^{11}}{\diagup}}$$

wherein $R^{11}$, $R^{12}$ and $R^{13}$ are independently selected from the group consisting of H, methyl, phenyl or trimethylsilyl.

12. The compound of claim 1 wherein $R^9$ and $R^{10}$ are both $$\text{———}\equiv\text{———}R^{14}$$

wherein $R^{14}$ is H, methyl, phenyl or trimethylsilyl.

13. A compound of the formula:

$$R^{15} \underset{R^{16}}{\overset{}{\diagdown}}=\underset{CH_3}{\overset{CH_3}{\underset{|}{\overset{|}{Si}}}}-O-\underset{CH_3}{\overset{CH_3}{\underset{|}{\overset{|}{Si}}}}-CB_{10}H_{10}C-\underset{CH_3}{\overset{CH_3}{\underset{|}{\overset{|}{Si}}}}-O-\underset{CH_3}{\overset{CH_3}{\underset{|}{\overset{|}{Si}}}}\underset{R^{17}}{\overset{R^{18}}{\diagup}}=$$

wherein at least one of $R^{15}$ and $R^{16}$ is H and the other is H or methyl, and wherein at least one of $R^{17}$ and $R^{18}$ is H and the other is H or methyl.

14. The compound of claim 13 wherein $R^{15}$, $R^{16}$, $R^{17}$ and $R^{18}$ are H.

15. A compound of the formula:

$$R^{19}\text{—}\equiv\text{—}\underset{CH_3}{\overset{CH_3}{\underset{|}{\overset{|}{Si}}}}-O-\underset{CH_3}{\overset{CH_3}{\underset{|}{\overset{|}{Si}}}}-CB_{10}H_{10}C-\underset{CH_3}{\overset{CH_3}{\underset{|}{\overset{|}{Si}}}}-O-\underset{CH_3}{\overset{CH_3}{\underset{|}{\overset{|}{Si}}}}\text{—}\equiv\text{—}R^{20}$$

wherein $R^{19}$ and $R^{20}$ are both H or are both phenyl.

16. The compound of claim 15 wherein $R^{19}$ and $R^{20}$ are H.

17. The compound of claim 15 wherein $R^{19}$ and $R^{20}$ are phenyl.

* * * * *